United States Patent [19]

Fairbanks

[11] Patent Number: 4,873,866

[45] Date of Patent: Oct. 17, 1989

[54] METHOD OF HYDROSTATIC WEIGHING AND KIT

[76] Inventor: Bert L. Fairbanks, 2306 22nd Avenue South, Lethbridge, Alberta, Canada, T1K 1J5

[21] Appl. No.: 33,771

[22] Filed: Apr. 3, 1987

[51] Int. Cl.$^4$ ............................................. G01N 9/08
[52] U.S. Cl. ..................................................... 73/437
[58] Field of Search ............... 73/437, 433, 32 R, 149, 73/450; 177/207

[56] References Cited

U.S. PATENT DOCUMENTS

| | | | |
|---|---|---|---|
| 3,045,496 | 7/1962 | Kraus | 73/450 |
| 4,144,749 | 3/1979 | Whitmore | 73/149 |
| 4,184,371 | 1/1980 | Brachet | 73/433 |
| 4,753,307 | 6/1988 | Muehlenbein | 177/207 |

OTHER PUBLICATIONS

J. H. Wilmore et al., "An Anthropometic Estimation of Body Density and Lean Body Weight in Young Men," *Journal of Applied Physiology*, vol. 27, No. 1, Jul. 1969, pp. 25–31.

J. H. Wilmore et al., "Predictability of Lean Body Weight Through Anthropometic Assessment in College Men," *Journal of Applied Physiology*, vol. 25, No. 4, Oct. 1968, pp. 349–355.

*Primary Examiner*—John Chapman
*Attorney, Agent, or Firm*—George H. Mortimer

[57] ABSTRACT

The invention is a method of hydrostatic weighing of a human body and a kit for use in hydrosatic weighing. The method comprises filling with water and closing a container which the person being weighed can grasp, having the person being weighed grasp the filled and closed container and sink himself in a pool of water, remove from the container a quantity of water just sufficient to suspend himself between the bottom of the pool and its surface when he has exhaled as much air as possible from his lungs, determine the weight of water needed to refill the container and determining the density of the water, e.g., by taking its temperature. The kit comprises a container with a screw cap which is capable of being grasped by a person being hydrostatically weighed, a graduated cylinder for determining the weight of the water required to refill the container after it has been adjusted by removal of water to suspend the person in water, a weight which is necessary if the person being weighed floats in water, and a thermometer to determine the density of the water being used for the hydrostatic weighing. A nose clip and data sheet may be included in the kit, if desired.

8 Claims, 1 Drawing Sheet

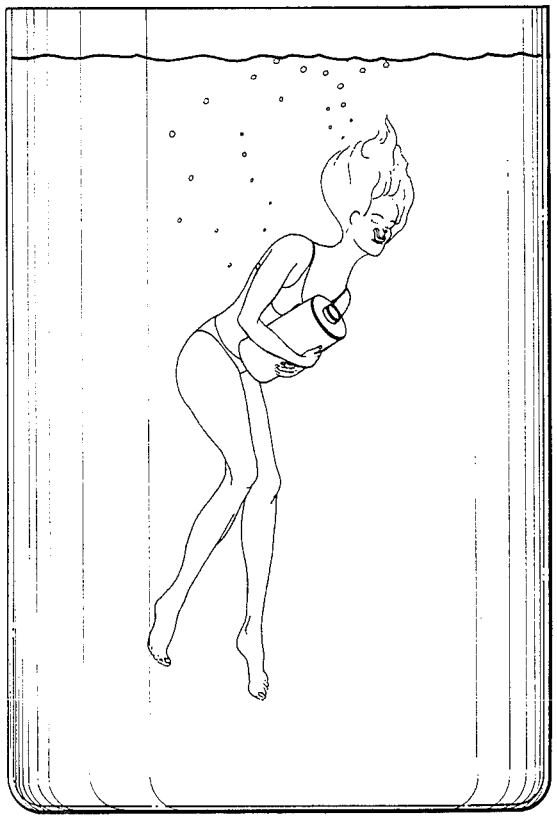

FIG. 1

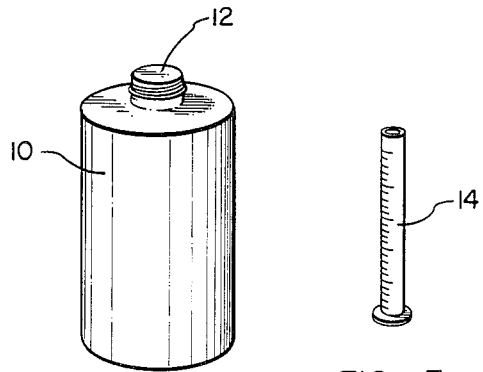

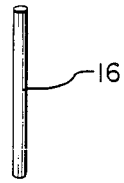

FIG. 4

FIG. 5

FIG. 6

DATA SHEET

Name _____    Date _____ 19 ___

Week #: _____ Time of Day: _____ a.m./p.m.

[ ] Medical Clearance                    [ ] Avoid Exercise - 3 Hrs. Prior to test
[ ] Avoid Large Meals - 3 Hrs. Prior to Test    [ ] Empty Bladder and Colon

| M/F | Sex |
| _____ yrs. | Age |
| _____ inches | Height |
| _____ lbs. | Weight |
| _____ C. | Water Temperature |
| _____ ml. | *Measurement |
| Y/N | External Weight |
| _____ | Steel Rod |
|  | 1 = 1670 |
|  | 2 = 3340 |
|  | 3 = 5010 |

_____ %    *Percent Body Fat
_____      *Less Body Mass
_____ lbs. *Density
_____ %    *Percent Fat Goal
_____ lbs. *Target Weight

*Record information on your Progress Log

FIG. 7

METHOD OF HYDROSTATIC WEIGHING AND KIT

INTRODUCTION

The present invention relates to a method for hydrostatic weighing and a kit for use in carrying out the method. More particularly it pertains to a method of performing the weighing of a human body underwater in a readily available, quiet pool of water with the kit of inexpensive, simple equipment.

BACKGROUND OF THE INVENTION

The serious human health problems which have their origins in obesity have been recognized in the medical profession for a number of years as evidenced by the flood of literature on the subject and by the number of so-called health centers which have proliferated in developed countries of the world for the purpose of assisting men and women to regain and retain a proper, healthful body weight and tone. Jack H. Whilmore and Albert R. Behnke in an article entitled PREDICTABILITY OF LEAN BODY WEIGHT THROUGH ANTHROPOMETRIC ASSESSMENT IN COLLEGE MEN published by JOURNAL OF APPLIED PHYSIOLOGY, Vol. 25, No. 4, October, 1968, cite twenty-three (23) literature references from which they summarize the problems, point out that obesity now appearing more frequently in childhood and early adolesence tends to persist into later life making it "highly desirable to assess lean body weight and its complement, percentage of body fat, at regular intervals throughout each individual's life beginning at an early age."

The same authors in an article entitled AN ANTHROPOMETRIC ESTIMATION OF BODY DENSITY AND LEAN BODY WEIGHT IN YOUNG MEN, published in JOURNAL OF APPLIED PHYSIOLOGY, Vol. 27, No. 1, July 1969, cite nineteen (19) literature references relating to methods used up to that time for assessing body fat and lean body weight in humans, including measurements of total body water, total body potassium, helium dilution, radiography and body density-specific gravity but point out that "they all share the common problems of requiring: (1) considerable time for a single determination, (2) relative elaborate and expensive equipment, and (3) rather complex procedures." They then report on their study to evaluate the predictability of body density and lean body weight from a sizable number of anthropometric measurements, such as skinfolds, diameters and circumferences but this approach has not solved the problems.

Attempts to solve the problems have been made by inventors who have obtained U.S. patents on their devices and methods among which are the following:

Taylor et al., U.S. Pat. No. 3,455,168. granted July, 15, 1969, for a complex mechanism for measuring fat content of animal tissue.

Fletcher et al., U.S. Pat. No. 3,769,834, granted Nov. 6, 1973, for a whole body measurement system including a special enclosed container for receiving a human body which is then subjected to changes in volume and pressure under isentropic conditions to determine body volume.

Whitmore, U.S. Pat. No. 4,144,749, granted Mar. 20, 1979, for a total body volume water comprising a large tank in which a human may sit and be completely immersed in water while determining the body volume Vogelman, U.S. Pat. No. 4,144,763, granted Mar. 20, 1979 for a non-invasive method of determining body fat using special apparatus comprising a pair of airtight chambers to measure the body volume.

Brachet, U.S. Pat. No. 4,184,371, granted Jan. 22, 1980, for a special apparatus for measuring the density of a body comprising a main chamber in which the body is positioned, an auxiliary chamber, a subsonic wave generator and measuring means.

Van Haren, U.S. Pat. No. 4,449,406, granted May 22, 1984, for a method and device for measuring the fat content of meat in a production line.

None of these devices or methods makes available to the public a simple, economical, readily available way of determining accurately the volume and density of a human body.

SUMMARY OF THE INVENTION

The present invention solves the problem of a prior art by providing a method of hydrostatic weighing of a human body in a readily available body of water such as a swimming pool, a pond, or the like, using a kit comprising inexpensive, simple equipment. For the purpose of this invention human bodies fall into two categories: (1) those which will sink and (2) those which will float in water. A container capable of being grasped by the person whose body density is being determined is filled with water and closed with a removable closure. A person in category (1) then removes just enough water so that when the immerses himself in a body of water with the container clasped to his body he will be suspended between the surface and bottom thereof. A person in category (2) has to add a sufficient weight to the container so that he can remove just enough water from it to suspend himself in a body of water between the surface and bottom thereof when he clasps the weighted container. The weight of water required to refill the container is then determined. Body density can be calculated from these data as described hereinafter.

BRIEF DESCRIPTION OF THE DRAWINGS

The method and kit of the invention will be described and illustrated by reference to the drawing in which:

FIG. 1 illustrates the position of a human body in a body of water during hydrostatic weighing;

FIGS. 2 through 7 show items which may comprise the contents of the kit which are:

a container as depicted in FIG. 2 which is capable of being grasped by a person as shown in FIG. 1 and it has such capacity as to hold an amount of water, and weights if necessary, just sufficient to suspend the body of the person grasping it above the bottom of a body of water an under the surface thereof when the person has exhaled the maximum amount of air from the lungs;

a water measuring device as depicted in FIG. 3, e.g., a graduate cylinder;

a weight as depicted in FIG. 4 that may be needed for hydrostatic weighing of very obese persons, a thermometer as depicted in FIG. 5 for measuring water temperature at the time of hydrostatic weighing;

a nose clip as depicted in FIG. 6 which a person may apply to the nose to asssist in holding the breath while submerged for a few seconds; and a suitable data sheet as depicted in FIG. 7 for recording the necessary information during the hydrostatic test.

DETAILED DESCRIPTION OF PREFERRED EMBODIMENTS OF THE INVENTION

The method of determining density of a human body in accordance with the invention comprises (A) filling with water a rigid container capable of being grasped by a person whose body density is being determined and sinking the person in a body of water, (B) removing water from said container until it contains just enough air (or water) stably to suspend the person grasping it in a body of water above the bottom and below the surface when air from the lungs has been exhaled, and (C) determining the weight of the water required to refill the container. From this information and the temperature of the water the density and percent fat of the body of the person can be calculated by well known formulae.

The essential items for the kit comprise the container, the water measuring device, the weight and the thermometer. The nose clip and data sheet are desirable but not essential.

People being weighed fall into two categories. In one category are persons having a body density greater than the water in which they are being hydrostatically weighed when air from their lungs has been exhausted so that they will sink to the bottom. In the other category are persons having a body density less than the water in which they are being hydrostatically weighed when air from their lungs has been exhausted so that they will float to the top. In hydrostatically weighting persons in the first catgegory, containers are readily avaiable which can be used as is but for hydrostatically weighing persons in the second category it is necessary to add weight to the container in order to use it in the method as described.

The container 10 used in the hydrostatic test can be an empty vinegar or bleach bottle or a specially made bottle of suitable material such as a high density polyethylene or polypropylene plastic, and the like. It must be sufficiently rigid that its shape is not changed substantially during its use in the hydrostatic weighing procedure and the word "rigid" as used herein is to be so construed. Glass containers can be used but are not preferred because of the danger of breaking the glass and producing dangerous fragments for bare feet of persons undergoing the hydrostatic test. The container is provided with a water-tight screw cap 12.

In making the hydrostatic test it is necessary to take into consideration the density of the filled container. One way to do this is first to fill the container with water, screw the cap on tightly, place it in the body of water in which the test is to be made, e.g., a swimming pool, a pond, or the like, and, if necessary, add a few marlbes, ball bearings or the like until the filled container is stably suspended in the body of water. No special tank or the like is necessary in carrying out the invention which greatly reduces the expense of the necessary equipment for the test. Persons in the first category then can be hydrostatically weighed using the container as thus prepared but for hydrostatically weighing persons in the second category it is necessary to add sufficient weight to the container, e.g., a steel rod as shown in FIG. 4, so that then the person or subject being weighed grasps it and makes the adjustment described below his body will be suspended between the bottom of the body of water and its surface.

The person or subject being tested should not eat or exercise within about three hours of the test and should either be naked or wear a tight fitting swim suit that will not entrap air. The body of water should be about waist deep. Grasping the container much as a baby would be held, as illustrated in FIG. 1 of the drawing, the subject being tested exhales as much air from the lungs as possible, holds the breath, crouches down and bends forward in the water for a few seconds. The nose clip may be used to assist the person to hold his breath for these few seconds if he finds it necessary or desirable. If the body of the subject is more dense than the water in the body of water, he will then sink to the bottom. The subject must then stand up, breath normally, remove the screw cap and pour out enough liquid so that when the subject again is immersed as described the body will remain suspended between the bottom and surface of the body of water as illustrated in FIG. 1 of the drawing. If the body of the subject is less dense than the water so that it floats, a sufficient weight such as a stainless steel bar 16 must be placed in the bottle to sink the subject. Water is then removed from the container to accomplish the described suspension of the human body and grasped container between the bottom and surface of the body of water.

The next step is to refill the bottle with a determined weight of water. This is preferably done from a graduated cylinder 14 but any comparable method can also be used, e.g., the container may be graduated, or enough water may be poured into the container to refill it from a vessel containing a weighed quantity of water which is then reweighed to determine the weight of the water required to refill the container. The weight of the water required to refill the container is the hydrostatic weight of the human body being tested. It is identical to the weight that would have been obtained by the use of an expensive hydrostatic weighing tank.

This completes the hydrostatic weighing process of the invention. It is advantageous to record the information obtained on a data sheet such as that shown in FIG. 7. The essentials are the indicated information about the subject being tested, the water temperature, the weight, if any, added to the container used in the test and the weight of the water required to refill the container. From these data the body density and percent fat content can be calculated using the known formulae for body density calculation from weight determined by prior art methods, e.g., as disclosed in the aforementioned article in volume 27 of the Journal of Applied Physiologoy.

The body density can be calculated from the formula $$D = Wa/(K - RV)$$

in which $D$=body density in grams per cubic centimeter, $Wa$=weight of the body in air in grams taken at the time of the test, $Ww$=weight of the body in grams in water as just determined, $K = Wa - Ww$ divided by the density of the water at the weighing temperature, and $RV$=the residual volume in cubic centimeters. Residual volume is the volume of air remaining in the lungs and respiratory tract after the strongest possible force of expiration. This volume may be determined in any convenient matter known in the art, e.g., with the use of an inert gas such as nitrogen.

The percent fat can be computed by the formula:

$$\% \text{ fat} = (4.570/D - 4.142) \times 100.$$

The following is an illustrative example of the calculations of body density and percentage of body fat.

Sex = male
Age = 50 years
Height = 72 inches = 182.88 centimeters
Weight in air = 170 pounds = 77110.7 grams.
Weight in water = 5.75 pounds = 2608.2 grams
Density of water at 25° C. = 0.99707 gram per cubic centimeter
$RV = 26 \times$ age in years $+ 110 \times$ height in inches $- 11 \times Wa$ in pounds $- 4570 = 2780$
$K = (77110.7 - 2608.2)/0.99707 = 74502.5/0.99707 = 74721.4338$
$D = 77110.7/(74721.4338 - 2780) = 77110.7/71941.4338 = 1.071853811$
% fat $= (4.570/1.071853811 - 4.142) \times 100 = (4.2636 - 4.142) \times 100 = 12.16\%$ Although the invention has been described and illustrated in connection with certain specific apparatus and procedures, modifications and variations can be resorted to without departing from the spirit and scope of the invention as defined in the following claims.

I claim:

1. A method of determining density of a person's body which comprises:
   A. filling with water and closing a rigid container capable of being grasped by the person whose body density is being determined and sinking the person and container in a body of water, adding, if necessary, a weight X to the container;
   B. removing water from said container until it contains just enough air to suspend the person grasping it in the body of water above the bottom and below the surface;
   C. determining the weight of water in grams required to refill the container, taking as the person's weight in grams in water (i) that weight where no weight X is added and (ii) that weight less weight X where added; and
   D. calculating the density of the person's body from the formula $D = Wa/(K)$ where Wa is the weight of the person in air in grams, $K = WA - Ww$ divided by the density of the water where Ww is the weight of the person's body in grams in water as determined in step C.

2. The method as set forth in claim 1 in which the person's body density is greater than the density of the water in which the measurement is being taken, the container is filled with water alone and closed, and the amount of water in the container is adjusted until the persons' body is suspended in the body of water while grasping the container as stated.

3. The method as set forth in claim 1 in which the person's body density is less than the density of water in which the measurment is being taken, adding sufficient weight to the container so that when it is filled with water and closed it will cause the person to sink to the bottom of the body of water, and adjust the amount of water in the container until the person's body is suspended in the body of water as stated.

4. A method as set forth in claim 1 in which the temperature of the water in the container and the body of water is taken in order to determine the density of the water in the container and in the body of water.

5. A method of determining the density of a person's body which comprises:
   A. filling with water and closing a rigid container capable of being grasped by the person whose body density is being determined and placing the container in a body of water;
   B. the person, immersing himself in the body of water, grasps and removes water from said container until it contains just enough air to suspend it and the person in the body of water above the bottom and below the surface when air from the lungs has been exhaled, adding weight X if necessary to obtain such suspension;
   C. determining the weight of water in grams required to refill the container, taking as the person's weight in grams in water (i) that weight where no weight X is added and (ii) that weight less weight X where added; and
   D. calculating the density of the person's body from the formula $D = Wa/(K)$ where Wa is the weight of the person in air in grams, $K = Wa - Ww$ divided by the density of the water where Ww is the weight of the person's body in grams in water as determined in step C.

6. The method as set forth in claim 5 in which the person's body density is greater than the density of the water in which the measurement is being taken and the partially filled container alone is capable of suspending the body of the person grasping the container as stated.

7. The method as set forth in claim 5 in which the density of the person's body is less than the density of the water in which the measurement is being taken, adding sufficient weight to the container to sink the body of the person when grasping the filled and closed container, and adjusting the amount of water in the closed container to suspend the person's body as stated.

8. A method as set forth in claim 5 in which the temperature of the water in the container and in the body of water is taken in order to determine the density of the water in the container and the body.

* * * * *